(12) United States Patent
Quadir

(10) Patent No.: US 7,416,567 B2
(45) Date of Patent: Aug. 26, 2008

(54) COSMETIC COMPOSITION FOR KERATINOUS SUBSTRATES WITH TRIARYLMETHANE COMPOUNDS

(75) Inventor: Murat Quadir, Scotch Plains, NJ (US)

(73) Assignee: L'Oreal, Paris (FR)

( * ) Notice: Subject to any disclaimer, the term of this patent is extended or adjusted under 35 U.S.C. 154(b) by 130 days.

(21) Appl. No.: 11/644,351

(22) Filed: Dec. 22, 2006

(65) Prior Publication Data

US 2008/0148495 A1   Jun. 26, 2008

(51) Int. Cl.
*A61Q 5/10*   (2006.01)
*C09B 11/02*   (2006.01)

(52) U.S. Cl. .................. 8/405; 8/426; 8/435; 8/551; 8/552; 8/554; 8/555; 8/557; 8/558; 564/321; 132/202; 132/208

(58) Field of Classification Search .............. 8/405, 8/426, 435, 551, 552, 554, 555, 557, 558; 564/321; 132/202, 208
See application file for complete search history.

(56) References Cited

U.S. PATENT DOCUMENTS

| | | | |
|---|---|---|---|
| 2,438,091 A | 3/1948 | Lynch | |
| 2,528,378 A | 10/1950 | Mannheimer | |
| 2,658,072 A | 11/1953 | Milton | |
| 3,589,578 A | 6/1971 | Kamphausen | |
| 3,836,537 A | 9/1974 | Boerwinkle et al. | |
| 3,929,678 A | 12/1975 | Laughlin et al. | |
| 4,031,307 A | 6/1977 | DeMartino et al. | |
| 4,128,631 A | 12/1978 | Lundmark et al. | |
| 4,165,367 A | 8/1979 | Chakrabarti | |
| 4,275,055 A | 6/1981 | Nachtigal et al. | |
| 4,311,695 A | 1/1982 | Starch | |
| 4,353,833 A | 10/1982 | Bruder et al. | |
| 4,477,635 A * | 10/1984 | Mitra | 525/437 |
| 5,750,742 A | 5/1998 | Schroder et al. | |
| 6,562,328 B2 | 5/2003 | Pereira et al. | |
| 2006/0021161 A1 | 2/2006 | Lagrange et al. | |

FOREIGN PATENT DOCUMENTS

| | | |
|---|---|---|
| EP | 0080976 | 6/1983 |
| EP | 0331833 | 9/1989 |
| EP | 1532970 | 5/2005 |
| FR | 1400366 | 5/1965 |
| FR | 2077143 | 10/1971 |
| FR | 2393573 | 1/1979 |
| GB | 1021400 | 3/1966 |
| GB | 1331819 | 9/1973 |
| WO | WO 9606139 | 2/1996 |
| WO | WO 2006097360 | 9/2006 |

OTHER PUBLICATIONS

English translation of the "Research Disclosure 43237 BASF" (Apr. 2000).*
Nikitakis et al, CTFA International Cosmetic Ingredient Dictionary, 1991, 4th edition, The Cosmetic, Toiletry, and Fragrance Association, Washington DC, USA.
Madore et al., "Water-Soluble Dimethicone Copolyol Waxes for Personal Care Industry," Presented at the 17th IFSCC International Congress Yokohama, Oct. 13-16, 1992, pp. 1-3, Dow Corning Corporation, Midland, USA.
McCutcheon's "Detergents and Emulsifiers," North American Edition 1986, McCutcheon Division, MC Publishing Co., Glen Rock, USA.
McCutcheon's "Functional Materials," North American Edition, vol. 2, 1992, McCutcheon Division, MC Publishing Co., Glen Rock, USA.
Pepe et al, CTFA International Cosmetic Ingredient Dictionary, 2002, 9th edition, The Cosmetic, Toiletry, and Fragrance Association, Washington DC, USA.
Schroder, Research Disclosure, Apr. 2000, No. 432, pp. 648-649, BASF Corporation.
Incroquat Behenyl 18-MEA, Personal Care, DS-152, May 10, 2000, pp. 1-7, Croda Inc., Parsippany, USA.

* cited by examiner

*Primary Examiner*—Eisa B Elhilo
(74) *Attorney, Agent, or Firm*—Maria Luisa Balasta; Francois Maniere; Steven Trzaska

(57) ABSTRACT

The invention relates to a method of imparting color onto keratinous substrates involving contacting said substrate with a composition comprising: at least one triarylmethane dye molecule chosen from polymeric triarylmethane dye molecules, copolymeric triarylmethane dye molecules, oligomeric triarylmethane dye molecules, and mixtures thereof; at least one film forming agent; and at least one solvent; and irradiating said substrate with a flash of light.

21 Claims, No Drawings

COSMETIC COMPOSITION FOR KERATINOUS SUBSTRATES WITH TRIARYLMETHANE COMPOUNDS

BACKGROUND OF THE INVENTION

Imparting a color change or color effect on hair can be done using permanent, semi-permanent or temporary hair coloring products. A permanent hair dye can produce a substantial change in the natural color and often uses oxidative dyes that penetrate into the hair fibers to permanently change the color of the hair. Permanent hair dyes can usually last up to 4 to 5 weeks. Permanent hair coloration can also include bleaching or lightening of the hair. On the other hand, a semi-permanent hair dye, which is also referred to as hair coating or hair glazing, may provide color for about six to twelve shampoos. This type of hair dye is gentler than a permanent dye because it does not contain peroxide. These products are in contrast to temporary hair coloring products which can either give a slight change to enhance the natural color of the hair or impart bold colors or "special effects" (such as green, blue, red and pink) to human hair. These types of hair dyes make use of dye molecules that are large enough so that they do not diffuse into the hair shaft, and therefore act on the exterior of the hair. Consequently, temporary hair dyes generally wash out after one or two shampoos. The advantages of using temporary hair dyes is that they are gentle on the hair and it gives the user the flexibility to change one's hair color as desired more frequently.

Polymeric, copolymeric and oligomeric triarylmethane (TAM) dyes are known for use in the coloring of textiles, plastics, and cellulose substrates. U.S. Pat. Nos. 5,750,742, 4,477,635, and 4,353,833, the entire content of which are hereby incorporated by reference, describe the use of this class of dye, which has an improved fastness towards light and may change in hue due to prolonged exposure. However, these references do not mention the use of these dyes in a cosmetics application. US2006/0021161 A1, the entire content of which is hereby incorporated by reference, describes the use of monomeric triarylmethane dyes for temporarily coloring the hair. This reference, however, does not discuss the use of oligomeric and/or polymeric and/or copolymeric triarylmethane dyes nor does it mention the use of a flash of light to impart a color change to keratinous substrates.

While numerous temporary hair dyes currently on the market are effective in imparting a range of colors to the hair, they are not designed to impart a change in color and enhanced shine as a result of exposure to a flash of light.

SUMMARY OF THE INVENTION

The invention relates to a process for imparting color onto a keratinous substrate involving:
a) providing a keratinous substrate;
b) providing a cosmetic composition containing:
   i) at least one triarylmethane dye molecule chosen from polymeric triarylmethane dye molecules, copolymeric triarylmethane dye molecules, oligomeric triarylmethane dye molecules, and mixtures thereof;
   ii) at least one film forming agent; and,
   iii) at least one solvent,
c) contacting the keratinous substrate with the cosmetic composition to form a treated keratinous substrate; and,
d) irradiating the treated keratinous substrate with a flash of light.

The present invention also provides for cosmetic compositions containing: at least one triarylmethane dye molecule chosen from polymeric triarylmethane dye molecules, copolymeric triarylmethane dye molecules, oligomeric triarylmethane dye molecules, and mixtures thereof; at least one film forming agent; and at least one solvent, wherein said compositions impart a change in color to keratinous substrates.

DETAILED DESCRIPTION OF THE INVENTION

Other than in the operating examples, or where otherwise indicated, all numbers expressing quantities of ingredients or reaction conditions are to be understood as being modified in all instances by the term "about".

As used herein, the expression "at least one" means one or more and thus includes individual components as well as mixtures/combinations.

"Cosmetically acceptable" means that the item in question is compatible with any keratin material. For example, "cosmetically acceptable medium" means a medium that is compatible with any keratinous substrate.

"Formed from," as used herein, means obtained from chemical reaction of, wherein "chemical reaction," includes spontaneous chemical reactions and induced chemical reactions. As used herein, the phrase "formed from", is open ended and does not limit the components of the composition to those listed, e.g., as component (i) and component (ii). Furthermore, the phrase "formed from" does not limit the order of adding components to the composition or require that the listed components (e.g., components (i) and (ii)) be added to the composition before any other components.

"Silicone compound," as used herein, includes, for example, silica, silanes, silazanes, siloxanes, and organosiloxanes; and refers to a compound comprising at least one silicon; wherein the silicone compound may be chosen from linear silicone compounds, branched silicone compounds, and cyclic silicone compounds; further wherein the silicone compound may optionally be substituted; and further wherein the silicone compound may optionally further comprise at least one heteroatom intercalated in the silicone chain, wherein the at least one heteroatom is different from the at least one silicon.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups.

The term "keratinous substrate" refers to human keratinous fiber, and may be chosen from, for example, hair, eyelashes, and eyebrows, as well as the stratum corneum of the skin and nails.

The terms "hair treatment composition," "cosmetic composition," and "composition," which are used interchangeably herein, refer to any products to be applied to keratinous substrates, especially hair, to impart hair shine, sheen, luster and color. Examples are hair mascara, spray, mousse, styling gel, leave-on conditioner, shampoo, conditioner, hair dye, permanent waving composition, hair care product, hair treatment product and hair styling product.

The terms "film forming agent" and "film forming polymer", which are used interchangeably herein, refers to any polymer that substantially forms a film on a substrate while providing one or more desirable properties such as good adherence to substrates, flexibility, good wearability, good drying time, non-tackiness, good retention, stain-resistance (transfer-resistance), desirable color, shine or tint and/or low migration over time, among other properties.

The term "solvent" refers to any substance that is useful in mixing, solubilizing, dispersing, suspending or emulsifying TAM-based dyes.

The term "propellant" refers to any gas (liquefiable gas or permanent gas) used to expel materials from an aerosol container.

The term "flash of light" refers to having a light power of 0.05 J/cm$^2$ and higher, a light wavelength of from 400 nm to 700 nm, a flash duration of 1.0 ms and greater, and a flash distance to the target of 1.0 cm and larger.

It has been found, entirely surprisingly and unexpectedly, that through the use of the present invention, it is possible to impart a change in color and an enhanced shine to a keratinous substrate upon exposure to a flash of light.

It is to be understood that both the foregoing general description and the following detailed description are exemplary and explanatory on and are not restrictive of the invention as claimed.

POLYMERIC, COPOLYMERIC AND OLIGOMERIC TRIARYLMETHANE DYES

Improvements are continuously being made on dyes in order to progress in various characteristics, such as color retention, wearability, and absorption of dye onto a substrate. Some common methods for improving dyes are by (a) altering the dye structure to increase the physical absorption of the dye onto the substrate, (b) providing functional groups on the dye that form covalent bonds with active sites on the substrate, or (c) changing the physical shape of the dye to provide improved mechanical retention of the dye by the substrate. An example of the second and third methods may be seen from the preparation of and use of oligomeric or polymeric or copolymeric dyes.

Structurally, triarylmethane pigments/dyes are derived from triphenylmethane or diphenylnaphthylmethane. In order to achieve the required spectral absorption properties that characterize these dyes, amine groups (primary, secondary, or tertiary) or hydroxyl groups must be present on the aromatic ring position para to the methane carbon. Amine substitutions are more prevalent than hydroxyl substitutions.

The polymeric or copolymeric triarylmethane dyes can have polyester, polycarbonate, polyurethane, or polyethyleneimine backbones. As used herein, "triarylmethane" includes aminotriarylmethane and aminotriaromaticmethane.

The polymeric or copolymeric triarylmethane dyes of the invention can have at least one arylamino unit of the general formula (I):

I $$-(CH_2)_a-CH_2-\overset{\oplus}{N}-CH_2-(CH_2)_b-O-\overset{X}{\overset{\|}{C}}-(Y)_c-(R)_d-(Y)_c-\overset{X}{\overset{\|}{C}}-O-]_e$$

with $R^2$, $R^3$, $R^4$, $R^5$, $Ar^1$, $Ar^2$, $(W)_f$, $Z^\ominus$ wherein a and b are independently zero or an integer having a value of 1 to 3;

X is oxygen or sulfur;

Y is oxygen or —NH—;

R is a divalent organic group selected from (1) aliphatic groups having 2 to 12 carbon atoms and up to 2 non-contiguous catenary groups selected from —O—, —S—, and —NR$^1$—, in which R$^1$ is lower alkyl group having one to four carbon atoms, (2) cycloaliphatic groups having 5 to 12 carbon atoms, optionally having one catenary —O—, —S—, or group therein, and (3) arylene groups having 6 to 12 carbon atoms; c, d, and e are independently zero or one, with the provisos that when e is zero, then a is zero, and when c is zero or Y is oxygen, then X is oxygen;

R$^2$, R$^3$, R$^4$, and R$^5$ are independently hydrogen, an auxochromic group, a bathochromic group, or R$^2$ and R$^3$ or R$^4$ and R$^5$ together are a benzo group optionally substituted by auxochromic groups or bathochromic groups;

Ar$^1$ and Ar$^2$ are independently aromatic groups having one or two 5- or 6-atom rings with conjugated unsaturation, the 5-atom rings having four carbon atoms and one of oxygen, sulfur, or nitrogen or three carbon atoms, one nitrogen, and one of oxygen or sulfur in the 1,3-position or nitrogen in the 1,2- or 1,3-position, the 6-atom rings having six carbon atoms, or five carbon atoms and one nitrogen, or four carbon atoms and two nitrogens in the 1,2-, 1,3-, or 1,4-position or three carbon atoms and three nitrogens in the 1,3,5-position, each group optionally substituted by auxochromic and bathochromic groups; and W is a divalent group selected from the group consisting of a coordinate bond, —O—, —S—, in which R$^6$ is hydrogen or a lower alkyl group having one to four carbon atoms and R$^7$ and R$^8$ are independently hydrogen or lower alkyl group having one to four carbon atoms;

f is zero or one; and

Z$^\ominus$ is an anion.

More particularly, Ar$^1$ and Ar$^2$ are independently aromatic groups selected from phenyl, furyl, thienyl, pyrryl, thiazolyl, oxazolyl, imidazolyl, pyrazolyl, pyridyl, pyrimidyl, pyrazinyl, pyridazinyl, and s-triazinyl and their benzo derivatives, each optionally substituted by auxochromic or bathochromic groups.

The polymeric aminotriarylmethane dyes of the invention can be copolymeric and contain up to 99.9 mol percent of units of a non-arylamino unit-containing polyester, polycarbonate, or polyurethane having the general formula in which R$^9$ is an alkylene group having 2 to 12 carbon atoms or polyoxyethylene, polyoxypropylene or polyoxybutylene having a molecular weight up to 3000 and X, Y, R, c, and d are the same as defined above.

The polymeric aminotriarylmethane dyes, therefore, can contain 0.1 to 100 mol percent of the arylamino unit.

Examples of suitable polymeric triarylmethane dyes may be found in U.S. Pat. No. 4,477,635, the entire content of which is hereby incorporated by reference.

Examples of suitable oligomeric triarylmethane dyes may be found in U.S. Pat. No. 5,750,742, the entire content of which is hereby incorporated by reference.

Non limiting examples of oligomeric triarylmethane-based dyes that may be used are as follows:

Basic Violet Acetate (Basazol C Violet PR 8055) with the following formula:

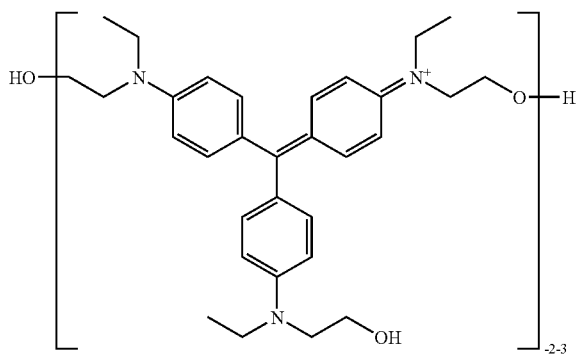

Basic Blue Acetate (Basazol C Violet PR 8056) with the following formula:

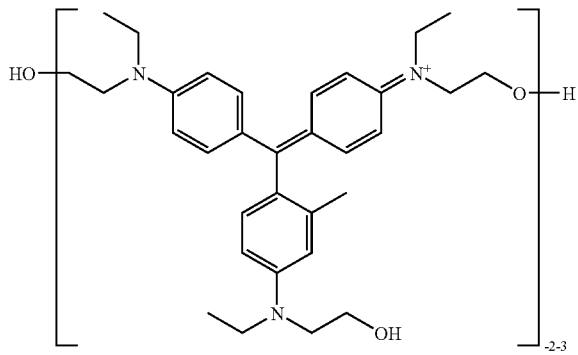

Such oligomeric triarylmethane dyes are available from BASF.

One skilled in the art would recognize that any polymeric triarylmethane dye, copolymeric triarylmethane dye, or oligomeric triarylmethane dye meeting the aforementioned objectives of the invention may be used in accordance with the present invention.

In a preferred embodiment of the present invention, the oligomeric triarylmethane dye used is Basazol C Violet PR 8055.

The amount of polymeric and/or copolymeric triarylmethane dyes and/or oligomeric triarylmethane dyes contained in the cosmetic composition of the present invention is not necessarily limited so long as sufficient material is provided to meet the objectives of the invention. However, in one embodiment of the present invention, the amount of polymeric and/or copolymeric triarylmethane dyes and/or oligomeric triarylmethane dyes ranges from 0.05% to 2% relative to the total weight of the cosmetic composition, preferably from 0.06 to 1.5%, even more preferably from 0.075% to 1% relative to the total weight of the cosmetic composition.

Film Forming Agents

As mentioned above, the composition disclosed herein comprises at least one film-forming agent. Film forming agents useful in the cosmetic composition of the present invention, in combination with the other ingredients, preferably provide the cosmetic composition with one or more desirable properties such as good adherence to substrates, flexibility, good wearability, good drying time, non-tackiness, good retention, stain-resistance (transfer-resistance), desirable color, shine or tint and/or low migration over time, among other properties. Preferably, film formation occurs when the solvent evaporates at a rate that allows a film to form continuously and substantially free from imperfections.

Any film forming agent may be suitable in the present invention. Preferably, the film forming agent used as a part of the present invention is chosen from film forming polymers and resins. The film forming polymers may be chosen from anionic polymers, amphoteric polymers, nonionic polymers, and cationic polymers.

The anionic film forming polymers employed in the current invention may be copolymers such as di-block, tri-block, multi-block and/or radial or star block copolymers. Mixtures of film formers may also be used. Indeed, the composition may comprise any one of an anionic film forming polymer or any mixture or blend of these film forming polymers.

Any anionic film forming polymer which provides one or more desirable properties as mentioned above can be used in the present invention. In one embodiment, the anionic film forming polymers used in accordance with the present invention include, but are not limited to, polyvinyl pyrrolidone, polyvinyl pyrrolidone/vinyl acetate, polyvinyl caprolactam, acrylates copolymer, acrylates/acrylamide copolymer, octylacrylamide/acrylates/butylaminoethyl methacrylate copolymer, vinyl acetate/crotonates/vinyl neodecanoate copolymer, diglycol/CHDM/isophthalates/SIP copolymer, acrylates/hydroyesters acrylates copolymer, PVP/vinylcaprolactam/DMAPA acrylates copolymer, methacrylol ethyl betaine/acrylates copolymer, AMO-acrylates copolymer, carboxyvinyl polymers, polyurethane dispersions, polyurethane polymers, polyurethane-14 (and) AMP-Acrylates copolymer, vinylpyrrolidone/vinylcaprolactam copolymer, vinylpyrrolidone/dimethylaminoethyl methacrylate copolymer, PPG-1/IPDI/DMPA copolymer, poly(styrene-b-2-hydroxyethylmethacrylate, poly(styrene-b-acrylic acid), poly(methylmethacrylate-b-acrylic acid), polyvinylpyrrolidone/polyvinylcaprolactam, polyvinylpyrrolidone/dimethylaminopropylmethacrylamide, polyvinylcaprolactam/dimethylaminopropylmethacrylamide, isobutylene ethylmaleimide/hydroxyethylmaleimide, polyvinyl-pyrrolidone/dimethylaminoethylmeth-acrylate, quaternized polyvinyl-pyrrolidone/dimethylaminoethylmethacrylate, polyvinylpyrrolidone/polyvinylcaprolactam/dimethyl-aminoethylmethacrylate, poly(vinylacetate/crotonates/vinylneodecanoate), ethylenecarboxamide/AMPSA/methacrylic acid polymer, hydroxymethylcellulose polymers, isobutylene/ethylmaleimide/hydroxymethylmaleimide copolymer, acrylamide/acrylamidopropanessulfonate/methacrylates/terpolymer, and AMP-acrylates/allyl methacrylate copolymer.

Non-limiting examples of the commercially available products of the anionic film forming polymer are Ultrastrong®, Aculyn® 22, Viscophobe® DB100, Balance® CR, Dermacryl® LT, Fixate® G100L, Avalure® AC-118, Avalure® Ac-210, Avalure® Ac-120, Carbotac® XPD-1811, Resyn® 28-2930, Mexomere® PW, Synthalen® K, Sepigel® 305, Simulgel® EG, Allianz® OPT, Acudyne® SCP, Aquaflex® FX-64, Luviset SI P.U.R.A., Luviset® P.U.R., Avalue® UR 425, Avalure® UR 450, and Eastman® AQ 55S In a preferred embodiment of the present invention, the film forming agent is selected from imide based or sulphonate based anionic film forming agent.

ANIONIC POLYMERS COMPRISING IMIDE GROUP

The anionic polymers comprising an imide group may for example, be chosen from polymers comprising alkylmaleimide, polysuccinimide, and hydroxyalkylmaleimide.

Examples of these polymers include: Isobutylene/ethylmaleimide/hydroxyethylmaleimide in solution of ethanol sold under the name Aquaflex® FX-64 by International Specialty Products (ISP); polysuccinimide sold under the name Rhodomer PSI by Rhodia; polysuccinimide partially (50%) modified; polyisobutylene succinimide sold under the name Hostacerin PIB by Clariant.

ANIONIC POLYMERS COMPRISING SULFONATE GROUP

The anionic polymers comprising a sulfonate group, may for example, be chosen from polymers comprising vinylsulfonic, styrenesulfonic, naphthalenesulfonic, or acrylamidoalkylsulfonic, 2-sulphoethyl methacrylate, acrylamido-2-methylpropanesulphonic acid.

These copolymers may be obtained by polymerization of at least one sulphonic acid group or a sulphonate group and of at least one monomer chosen from the group consisting of:

a) linear, branched or cyclic vinyl esters;

b) linear, branched or cyclic (meth)acrylic acid esters;

c) mono- or disubstituted linear, branched or cyclic (meth) acrylic acid amides, d) styrene, α-methylstyrene or substituted styrene.

Non-limiting examples of these polymers include:

polyvinylsulfonic acid salts having a molecular weight ranging from 1000 to 100,000, and copolymers with an unsaturated comonomer such as acrylic or methacrylic acids and esters thereof, as well as acrylamide and derivatives thereof, and vinyl ethers and vinylpyrrolidone;

polystyrenesulfonic acid salts such as the sodium salts sold, for example, under the name Flexan 130 by National Starch. These compounds are described in Patent No. FR-A-2 198 719; and polyacrylamidosulfonic acid salts such as those mentioned in U.S. Pat. No. 4,128,631, and for example, polyacrylamidoethylpropanesulfonic acid salt sold, for example, under the name Acudyne™ SCP by Rohm and Haas Company.

AMPHOTERIC FILM FORMING POLYMERS

The amphoteric film-forming polymers which can be used in accordance with the invention can be chosen from polymers comprising B and C units distributed randomly in the polymer chain, where B denotes a unit deriving from a monomer comprising at least one basic nitrogen atom and C denotes a unit deriving from an acidic monomer comprising one or more carboxyl or sulpho groups or else B and C can denote groups deriving from zwitterionic carboxybetaine or sulphobetaine monomers; B and C can also denote a cationic polymer chain comprising primary, secondary, tertiary or quaternary amine groups, in which at least one of the amine groups carries a carboxyl or sulpho group connected via a hydrocarbonaceous radical, or else B and C form part of a chain of a polymer comprising an α,β-dicarboxy-ethylene unit, one of the carboxyl groups of which has been reacted with a polyamine comprising one or more primary or secondary amine groups.

The most particularly preferred amphoteric film-forming polymers corresponding to the definition given above are chosen from the following polymers:

(1) polymers resulting from the copolymerization of a monomer derived from a vinyl compound carrying a carboxyl group, such as more particularly acrylic acid, methacrylic acid, maleic acid or .alpha.-chloracrylic acid, and of a basic monomer derived from a substituted vinyl compound comprising at least one basic atom, such as more particularly dialkylaminoalkyl methacrylate and acrylate or dialkylaminoalkylmethacrylamide and -acrylamide. Such compounds are disclosed in U.S. Pat. No. 3,836,537.

(2) polymers comprising units deriving:

a) from at least one monomer chosen from acrylamides or methacrylamides substituted on the nitrogen by an alkyl radical, b) from at least one acidic comonomer comprising one or more reactive carboxyl groups, and from at least one basic comonomer, such as esters comprising primary, secondary, tertiary and quaternary amine substituents of acrylic and methacrylic acids and the quaternization product of dimethylaminoethyl methacrylate with dimethyl or diethyl sulphate.

The more particularly preferred N-substituted acrylamides or methacrylamides according to the invention are the groups in which the alkyl radicals comprise from 2 to 12 carbon atoms and more particularly N-ethylacrylamide, N-tert-butylacrylamide, N-tert-octylacrylamide, N-octylacrylamide, N-decylacrylamide or N-dodecylacrylamide, and the corresponding methacrylamides.

The acidic comonomers are more particularly chosen from acrylic, methacrylic, crotonic, itaconic, maleic or fumaric acids and alkyl monoesters having 1 to 4 carbon atoms of maleic or fumaric acids or anhydrides.

The preferred basic comonomers are aminoethyl, butylaminoethyl, N,N'-dimethylaminoethyl or N-tert-butylaminoethyl methacrylates.

Use is particularly made of the copolymers for which the CTFA name (4th Ed., 1991) is Octylacrylamide/acrylates/butylaminoethyl methacrylate copolymer, such as the products sold under the name Amphomer or Lovocryl 47 by the company National Starch.

(3) partially or completely alkylated and crosslinked polyaminoamides.

(4) polymers comprising zwitterionic units of formula:

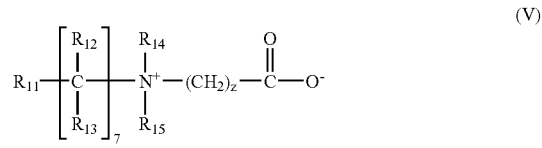

(V)

in which $R_{11}$ denotes a polymerizable unsaturated group, such as an acrylate, methacrylate, acrylamide or methacrylamide group, y and z represent an integer from 1 to 3, $R_{12}$ and $R_{13}$ represent a hydrogen atom or methyl, ethyl or propyl, and $R_{14}$ and $R_{15}$ represent a hydrogen atom or an alkyl radical such that the sum of the carbon atoms in $R_{14}$ and $R_{15}$ does not exceed 10.

The polymers comprising such units can also comprise units derived from non-zwitterionic monomers, such as dimethyl- or diethylaminoethyl acrylate or methacrylate or alkyl acrylates or methacrylates, acrylamides or methacrylamides, or vinyl acetate.

Mention may be made, by way of example, of the methyl methacrylate/methyl dimethylcarboxymethylammonioethyl methacrylate copolymer, such as the product sold under the name Diaformer Z301 by the company Sandoz.

(5) polymers derived from chitosan (6) polymers derived from the N-carboxyalkylation of chitosan, such as the N-(carboxymethyl)chitosan or the N-(carboxybutyl)chitosan sold under the name "Evalsan" by the company Jan Dekker.

(7) polymers corresponding to the general formula (VI), for example disclosed in French Patent 1,400,366:

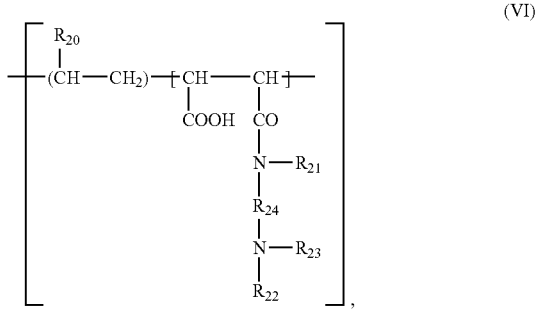

(VI)

in which $R_{20}$ represents/a hydrogen atom or a $CH_3$ O $CH_3$ $CH_2$ O or phenyl radical, $R_{21}$ denotes hydrogen or a lower alkyl radical such as methyl or ethyl, $R_{22}$ denotes hydrogen or a lower alkyl radical such as methyl or ethyl and $R_{23}$ denotes a lower alkyl radical such as methyl or ethyl or a radical corresponding to the formula: $-R_{24}-N(R_{22})_2$, $R_{24}$ representing a $-CH_2-CH_2-$, $-CH_2-CH_2-CH_2-$ or $-CH_2-CH(CH_3)-$ group and $R_{22}$ having the meanings mentioned above, and the higher homologues of these radicals comprising up to 6 carbon atoms.

(8) amphotericpolymers of the -D-X-D-X- type chosen from:

a) polymers obtained by reaction of chloracetic acid or sodium chloracetate with compounds comprising at least one unit of formula:

-D-X-D-X-D- (VII')

where D denotes a radical and X denotes the symbol E or E', E or E', which are identical or different, denote a bivalent radical which is a straight- or branched-chain alkylene radical comprising up to 7 carbon atoms in the main chain which is unsubstituted or substituted by hydroxyl groups and which can additionally comprise oxygen, nitrogen or sulphur atoms or 1 to 3 aromatic and/or heterocyclic rings; the oxygen, nitrogen and sulphur atoms being present in the form of ether, thioether, sulphoxide, sulphone, sulphonium, alkylamine or alkenylamine groups or hydroxyl, benzylamine, amine oxide, quaternary ammonium, amide, imide, alcohol, ester and/or urethane groups.

b) polymers of formula:

-D-X-D-X- (VII')

where D denotes a radical and X denotes the symbol E or E' and E' at least once, E having the meaning indicated above and E' is a bivalent radical which is a straight- or branched-chain alkylene radical having up to 7 carbon atoms in the main chain which is substituted or unsubstituted by one or more hydroxyl radicals and which comprises one or more nitrogen atoms, the nitrogen atom being substituted by an alkyl chain optionally interrupted by an oxygen atom and necessarily comprising one or more carboxyl functional groups and one or more hydroxyl functional groups and betainized by reaction with chloracetic acid or sodium chloracetate.

(9) ($C_1$-$C_5$)alkyl vinyl ether/maleic anhydride copolymers which is partially modified by semiamidation with an N,N-dialkylaminoalkylamine, such as N,N-dimethylaminopropylamine, or by semiesterification with an N,N-dialkanolamine. These copolymers can also comprise other vinyl comonomers, such as vinylcaprolactam.

The particularly preferred amphoteric film-forming polymers according to the invention are those of the family (3), such as the copolymers with the CTFA name of Octylacrylamide/acrylates/butylaminoethyl methacrylate copolymer, such as the products sold under the names Amphomer, Amhomer LV 71 or Lovocryl 47 by the company National Starch, and those of the family (4), such as methyl methacrylate/methyl dimethylcarboxymethylammonioethyl methacrylate copolymer, for example sold under the name Diaformer Z301 by the company Sandoz.

NON-IONIC FILM FORMING POLYMERS

Nonionic film-forming polymers which may be mentioned, for example, include:

cellulose polymers such as hydroxyethylcellulose, hydroxypropylcellulose, hydroxypropylethylcellulose and ethylhydroxyethylcellulose;

acrylic ester polymers or copolymers, such as polyacrylates or polymethacrylates;

vinyl polymers, such as polyvinylpyrrolidones and copolymers of vinylpyrrolidone and of vinyl acetate; polyvinyl alcohol;

polyesters, polyamides and epoxy ester resins;

polyurethane, polyurethane-polyvinylpyrrolidone, polyester-polyurethane, polyether-polyurethane, polyurea, and polyurea/polyurethane polymers, polymers of natural origin, which are optionally modified, such as gum arabics, guar gum, xanthan derivatives, and karaya gum;

and mixtures thereof.

The composition may comprise a polyoxyalkylenated silicone, chosen from silicones comprising a pendant or terminal polyoxyalkylenated chain, or alternatively a polyoxyalkylenated block. Polyoxyalkylenated chains or blocks which may be mentioned include polyoxyethylenated or polyoxypropylenated chains or blocks. Suitably, the polyoxyalkylenated silicone can be a (di)methicone copolyol.

In addition, some of these silicones are described, for example, in U.S. Pat. No. 4,311,695, the disclosure of which is incorporated by reference herein.

A number of polyoxyalkylenated silicones were presented in particular by Dow Corning during the 17 th international congress of the IFSCC in October 1992 and are reported in the article Water-Soluble Dimethicone Copolyol Waxes for Personal Care Industry by Linda Madore et al., pages 1 to 3. Those described in European Patent Application No. EP-A-331 833, the disclosure of which is incorporated by reference herein.

These polyoxyalkylenated silicones are polydimethylsiloxanes (PDMSs) comprising one or more water-soluble ether functions (oxyalkylene, such as oxyethylene and/or oxypropylene).

Such polyoxyalkylenated silicones are sold by the company Goldschmidt under the names ABIL B8851, ABIL B88183, ABIL WE09, ABIL EM90 and ABIL EM97. Mention may also be made of the compounds KF 351 to 354 and KF 615 A sold by Shin Etsu, or DMC 6038 sold by Wacker.

The dimethicone copolyol derivatives which can be used include, for example, dimethicone copolyols containing a phosphate, sulphate, myristamide propyldimethylammonium chloride, stearate, amine, and glycomodified groups, to name a few. Dimethicone copolyol derivatives which can be used include those compounds sold by Siltech under the names SILPHOS A100, SILTECH AMINE 65, SILWAX WDIS, and MYRISTAMIDO SILICONE QUAT, or by Phoenix under the name PECOSIL PS 100.

The derivatives sold by Wacker under the name BELSIL DMC6031, or by Dow Corning under the name 2501 cosmetic wax can also be used.

Suitably, polyoxyalkylenated silicone can be nonionic.

The polyoxyalkylenated silicones which may be used include, for example, those sold Dow Corning under the trade name Q2-5220 and by Rhône-Poulenc (now Aventis Pharma S.A.) under the name MIRASIL DMCO.

CATIONIC FILM FORMING POLYMERS

The cationic film-forming polymers which can be used according to the present invention are preferably chosen from polymers comprising primary, secondary, tertiary and/or quaternary amine groups forming part of the polymer chain or directly bonded to the latter and having a molecular weight of between 500 and approximately 5,000,000 and preferably between 1000 and 3,000,000.

Mention may more particularly be made, among these polymers, of the following cationic polymers:

homopolymers or copolymers derived from acrylic or methacrylic esters or amides. These copolymers may additionally comprise one or more units deriving from comonomers which can be chosen from the family of acrylamides, methacrylamides, diacetone acrylamides, acrylamides and methacrylamides substituted on the nitrogen by lower alkyls, acrylic or methacrylic acids and their esters, vinyllactams, such as vinylpyrrolidone or vinyl-caprolactam, or vinyl esters.

Thus, mention may be made of copolymers of acrylamide and of dimethylaminoethyl methacrylate quaternized with dimethyl sulphate or with a dimethyl halide, such as that sold under the name Hercofloc by the company Hercules, copolymers of acrylamide and of methacryloyloxyethyltrimethylammonium chloride which is disclosed, for example, in Patent Application EP-A-080,976 and sold under the name Bina Quat P 100 by the company Ciba-Geigy, the copolymer of acrylamide and of methacryloyloxyethyltrimethylammonium methyl sulphate sold under the name Reten by the company Hercules, optionally quaternized vinylpyrrolidone/dialkylaminoalkyl acrylate or methacrylate copolymers, such as the products sold under the name "Gafquat" by the company ISP, such as, for example, "Gafquat 734" or "Gafquat 755", or the products named "Copolymer 845, 958 and 937". These polymers are disclosed in detail in French Patents 2,077,143 and 2,393,573, dimethylaminoethyl methacrylate/vinylcaprolactam/vinylpyrrolidone terpolymers, such as the product sold under the name Gaffix VC 713 by the company ISP, and the quaternized dimethylaminopropyl methacrylamide/vinylpyrrolidone copolymer, such as the product sold under the name "Gafquat HS 100" by the company ISP.

quaternized polysaccharides, disclosed more particularly in U.S. Pat. Nos. 3,589,578 and 4,031,307, such as guar gums comprising cationic trialkylammonium groups.

Such products are sold in particular under the trade names Jaguar C13 S, Jaguar C15 and Jaguar C17 by the company Meyhall.

quaternary copolymers of vinylpyrrolidone and of vinylimidazole, such as the products sold by BASF under the name Luviquat FC;

chitosans or their salts; the salts which can be used are in particular chitosan acetate, lactate, glutamate, gluconate or pyrrolidonecarboxylate.

Mention may be made, among these compounds, of the chitosan having a degree of deacetylation of 90.5% by weight sold under the name Kytan Crude Standard by the company Aber Technologies or the chitosan pyrrolidonecarboxylate sold under the name Kytamer PC by the company Amerchol.

The anionic film-forming polymers generally used are polymers comprising groups derived from carboxylic, sulphonic or phosphoric acid and have a molecular weight of between approximately 500 and 5,000,000.

The carboxyl groups are contributed by unsaturated mono- or dicarboxylic acid monomers such as those corresponding to the formula:

$$\begin{array}{c} R_7 \\ \phantom{R}\diagdown \\ \phantom{RR}C=C \\ \phantom{R}\diagup \phantom{RR} \diagdown \\ R_8 \phantom{RRRR} R_9 \end{array} \begin{array}{c} (A_1)_n-COOH \\ \phantom{XXXXXX} \end{array} \qquad (II)$$

in which n is an integer from 0 to 10, A1 denotes a methylene group, optionally bonded to the carbon atom of the unsaturated group or to the neighboring methylene group when n is greater than 1 via a heteroatom, such as oxygen or sulphur, $R_7$ denotes a hydrogen atom or a phenyl or benzyl group, $R_8$ denotes a hydrogen atom or a lower alkyl or carboxyl group, and $R_9$ denotes a hydrogen atom, a lower alkyl group or a —$CH_2$—COOH, phenyl or benzyl group.

In the abovementioned formula, a lower alkyl radical preferably denotes a group having 1 to 4 carbon atoms and in particular methyl and ethyl.

The cationic film-forming polymers which can be used according to the present invention are preferably chosen from polymers comprising primary, secondary, tertiary and/or quaternary amine groups forming part of the polymer chain or directly bonded to the latter and having a molecular weight of between 500 and approximately 5,000,000 and preferably between 1000 and 3,000,000.

Mention may more particularly be made, among these polymers, of homopolymers or copolymers derived from acrylic or methacrylic esters or amides Depending on the application, the amount of film forming agent in the present invention may vary considerably. One of skill in the art will be able to determine the useful concentration of film forming agent depending on the application, shine and transfer resistance properties desired.

In one embodiment of the present invention, the amount of the film forming agent is present in an amount from 0.5% to 20% relative to the total weight of the cosmetic composition, preferably from 1.0% to 10% relative to the total weight of the composition, and more preferably from 2% to 5% relative to the total weight of the composition.

SOLVENT

The present invention contains at least one solvent. The solvent used in accordance with the present invention will be chosen by a one of ordinary skill in the art in order to prepare a cosmetic composition which has the desired properties previously mentioned. One of ordinary skill in the art will be able to determine a solvent based on the properties of the polymeric or copolymeric triarylmethane dye and/or oligomeric triarylmethane dye, the film forming agent, and others ingredients.

As mentioned above, the solvent is any substance that is useful in mixing, solubilizing, dispersing, suspending, or emulsifying triarylmethane dyes of the cosmetic composition.

In one embodiment of the invention, the solvent is selected from an organic solvent or water or a mixture thereof. In another embodiment of the invention, the solvent is selected from an alcohol or water or a mixture thereof.

In some embodiments, the alcohols that may be utilized include $C_1$ to $C_{20}$ straight chain, branched, cyclic, or aromatic alcohols, including, but not limited to, methanol, ethanol, propanol, butanol, tert-butanol, isopropanol, or benzyl alcohol or mixtures thereof.

In further embodiments, fatty alcohols derived from natural fats and/or oils including, but not limited to, 1-dodecanol or 1-octadecanol may be utilized in accordance with the present invention.

In yet other embodiments, hydrocarbons useful as a solvent in accordance with the present invention include, but are not limited to $C_1$-$C_{20}$ alkanes that may be straight, branched cyclic, or aromatic, mineral oils, mineral solvents, mineral spirits, petroleum, waxes, synthetic hydrocarbons, animal oils, vegetable oils, and mixtures thereof. In some embodiments, the solvent may be isododecane or a light paraffinic solvent. In other embodiments, the solvent may be a non-hydrocarbon solvent such as amyl acetate, buyl acetate, isobutyl acetate, ethyl acetate, propyl acetate or isopropyl acetate.

In a preferred embodiment, the solvent is ethanol, water or a mixture of ethanol and water.

The amount of solvent contained in the cosmetic composition of the present invention is not necessarily limited so long as sufficient material is provided to meet the objectives of the invention. However, in one embodiment of the present invention, the amount of solvent ranges from about 75% to about 99% with respect to the total weight of the composition, and preferably from about 80% to about 95% relative to the total weight of the composition.

SURFACTANTS

The present invention may optionally include at least one surfactant. The surfactants that may be included in accordance with the present invention include anionic, cationic, non-ionic, amphoteric and zwitterionic surfactants or mixtures thereof.

In a preferred embodiment of the present invention, the surfactant is chosen from an anionic surfactant. In another preferred embodiment of the present invention, the surfactant is an alkyl ether sulphate. In yet another preferred embodiment of the present invention, the surfactant is Empicol® BSD 52, which is commercially available from Huntsman Performance Products, Texas, U.S.A.

The surfactant used in accordance with the present invention, when present at all, is present in an amount ranging from about 0.05% to about 5% relative to the total weight of the composition, preferably from about 0.1% to about 3% relative to the total weight of the composition. These amounts can vary depending upon the type of surfactant.

ANIONIC SURFACTANTS

The compositions of the invention may include various anionic surfactants. Several examples of suitable anionic surfactants are disclosed in U.S. Pat. No. 3,929,678, which is incorporated herein by reference. Further examples of suitable anionic surfactants include alkoyl isethionates, and alkyl ether sulfates.

The alkoyl isethionates typically have the formula RCO—OCH$_2$CH$_2$—SO$_3$M, wherein R is $C_{10}$-$C_{30}$ alkyl, and M is a water-soluble cation, such as ammonium, sodium, potassium, or triethanolamine. The examples of suitable isethionates include ammonium cocoyl isethionate, sodium cocoyl isethionate, sodium lauroyl isethionate, sodium stearoyl isethionate, and mixtures thereof. Preferred for used herein are ammonium cocoyl isethionate, sodium cocoyl isethionate, and mixtures thereof.

The alkyl ether sulfates typically have the formulas ROSO$_3$M and RO(C$_2$H$_4$O)$_x$SO$_3$M, where R is $C_{10}$-$C_{30}$ alkyl, x varies from about 1 to about 10, and M is a water-soluble cation such as ammonium, sodium, potassium and triethanolamine.

Yet another suitable class of anionic surfactants are alkali metal salts of $C_8$-$C_{30}$ carboxylic acids and alkylsulfonates of the formula $R_1$—SO$_3$M (where $R_1$ is $C_8$-$C_{30}$ alkyl; preferably, $C_{12}$-$C_{22}$ alkyl, and M is a cation), including succinamates, and $C_{12}$-$C_{24}$ olefin sulfonates and carboxylates.

CATIONIC SURFACTANTS

Many cationic surfactants are known in the art, and almost any cationic surfactant having at least one long chain alkyl group of about 10 to 24 carbon atoms is suitable in the present invention. Cationic surfactants include ammonium quats and fatty amines.

AMMONIUM QUATS

The compositions of the invention may include quaternary ammonium cationic surfactants of the formula

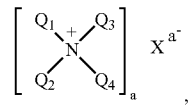

where X and a are as previously described, $Q_1$ is $C_{12}$-$C_{22}$ alkyl, $C_{12}$-$C_{22}$ alkyl amido $C_1$-$C_6$ alkylene, $C_{12}$-$C_{22}$ alkylhydroxy; $Q_2$ is $C_{12}$-$C_{22}$ alkyl, $C_{12}$-$C_{22}$ alkyl amido $C_1$-$C_6$ alkylene, $C_{12}$-$C_{22}$ alkylhydroxy, benzyl, or $C_1$-$C_6$ alkyl; $Q_3$ and $Q_4$ are independently $C_1$-$C_6$ alkyl or benzyl.

Examples of suitable quaternary ammonium surfactants include cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof.

Additional quaternary ammonium salts include those wherein the $C_{12}$-$C_{22}$ alkyl is derived from a tallow fatty acid or from a coconut fatty acid. Examples of quaternary ammonium salts derived from these tallow and cococut sources include ditallow dimethyl ammonium chlroide, ditallow dimehtyl ammonium methyl sulfate, di(hydrogenated tallow) dimethyl ammonium chloride, di(hydrogenated tallow)dimethyl ammonium acetate, ditallow dipropyl ammonium phosphate, ditallow dimethyl ammonium nitrate, di(coconutalkyl) dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl(myristyl acetate)ammonium chloride, stearamidopropyl dimethyl cetearyl ammonium tosylate, stearamidopropyl dimethyl ammonium chloride, stearamidopropyl dimethyl ammonium lactate, and mixtures thereof.

More preferred quaternary ammonium surfactants are dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldimonium ethosulfate, stearamidopropyl dimethyl(myristyl acetate)ammonium chloride, stearamidopropyl dimethyl cetearyl ammonium tosylate, stearamidopropyl dimethyl ammonium chloride, stearamidopropyl dimethyl ammonium lactate, and mixtures thereof.

FATTY AMINES

The compositions of the invention may also include salts of primary, secondary and tertiary $C_{12}$-$C_{22}$ amines. Examples of such suitable amines include stearamido propyl dimethyl amine, diethyl amino ethyl stearamide, dimethyl stearamine, dimethyl soyamine, soyamine, tri(decyl)amine, ethyl stearylamine, ethoxylated stearylamine, dihydroxyethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Some cationic amine surfactants useful in the compositions of the present invention are disclosed in U.S. Pat. No. 4,275,055, incorporated by reference herein.

NON-IONIC SURFACTANTS

The compositions of the invention may also include various non-ionic surfactants.

In general, nonionic surfactants having a Hydrophilic-Lipophilic Balance (HLB) of 4 or more, preferably from 4 to 20, are contemplated for use by the present invention. Nonlimiting examples of nonionic surfactants useful in the compositions of the present invention are disclosed in McCutcheon's "Detergents and Emulsifiers," North American Edition (1986), published by Allured Publishing Corporation; and McCutcheon's "Functional Materials," North American Edition (1992); both of which are incorporated by reference herein in their entirety.

Examples of nonionic surfactants useful herein include, but are not limited to, alkoxylated derivatives of the following: fatty alcohols, alkyl phenols, fatty acids, fatty acid esters and fatty acid amides, wherein the alkyl chain is in the $C_{12}$-$C_{50}$ range, preferably in the $C_{16}$-$C_{40}$ range, more preferably in the $C_{24}$ to $C_{40}$ range, and having from about 1 to about 110 alkoxy groups. The alkoxy groups are selected from the group consisting of $C_2$-$C_6$ oxides and their mixtures, with ethylene oxide, propylene oxide, and their mixtures being the preferred alkoxides. The alkyl chain may be linear, branched, saturated, or unsaturated. Of these alkoxylated non-ionic surfactants, the alkoxylated alcohols are preferred, and the ethoxylated alcohols and propoxylated alcohols are more preferred. The alkoxylated alcohols may be used alone or in mixtures thereof. The alkoxylated alcohols may also be used in mixtures with those alkoxylated materials disclosed herein-above.

Other representative examples of such ethoxylated fatty alcohols include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) steareth-10 (a stearyl alcohol ethoxylate having an average degree of ethoxylation of 10), and steareth-2 (a stearyl alcohol ethoxylate having an average degree of ethoxylation of 2), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), oleth-3 (an oleyl ethoxylate having an average degree of ethoxylation of 3), oleth-5 (an oleyl ethoxylate having an average degree of ethoxylation of 5), and oleth-20 (an oleyl ethoxylate having an average degree of ethoxylation of 20), and other derivatives and mixtures of the preceding.

Also available commercially are Brij® nonionic surfactants from Uniqema, Paterson, N.J. Typically, Brij® is the condensation products of aliphatic alcohols with from about 1 to about 54 moles of ethylene oxide, the alkyl chain of the alcohol being typically a linear chain and having from about 8 to about 22 carbon atoms, for example, Brij 72 (i.e., Steareth-2) and Brij 76 (i.e., Steareth-10).

Also useful herein as nonionic surfactants are alkyl glycosides, which are the condensation products of long chain alcohols, e.g. $C_{8-30}$ alcohols, with sugar or starch polymers. These compounds can be represented by the formula (S)n—O—R wherein S is a sugar moiety such as glucose, fructose, mannose, galactose, and the like; n is an integer of from about 1 to about 1000, and R is a $C_{8-30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a $C_{8-20}$ alkyl group, and n is an integer of from about 1 to about 9. Commercially available examples of these surfactants include decyl polyglucoside (available as APG® 325 CS) and lauryl polyglucoside (available as APG® 600CS and 625 CS), all the above-identified polyglucosides APG® are available from Cognis, Ambler, Pa. Also useful herein are sucrose ester surfactants such as sucrose cocoate and sucrose laurate.

Other nonionic surfactants suitable for use in the present invention are glyceryl esters and polyglyceryl esters, including but not limited to, glyceryl monoesters, preferably glyceryl monoesters of $C_{16}$-$C_{22}$ saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of $C_{16}$-$C_{22}$ saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. Preferable are sorbitan esters of $C_{16}$-$C_{22}$ saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from ICI Specialty Chemicals, Wilmington, Del.), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Also suitable for use herein are alkoxylated derivatives of glyceryl esters, sorbitan esters, and alkyl polyglycosides, wherein the alkoxy groups is selected from the group consisting of $C_2$-$C_6$ oxides and their mixtures, with ethoxylated or propoxylated derivatives of these materials being the preferred. Nonlimiting examples of commercially available ethoxylated materials include TWEEN® (ethoxylated sorbitan mono-, di- and/or tri-esters of $C_{12}$ to $C_{18}$ fatty acids with an average degree of ethoxylation of from about 2 to about 20).

AMPHOTERIC AND ZWITTERIONIC SURFACTANS

The compositions of the invention may also include zwitterionic and amphoteric surfactants. Suitable amphoteric and zwitterionic surfactants are, for example, derivatives of mono- or di-$C_8$-$C_{24}$ secondary and tertiary amines, such as alkyl imino acetates, carboxylates, sulfonates, sulfates, phosphates, and phosphonates, including iminodialkanoates and aminoalkanoates of the formulas $RN(CH_2)_m CO_2 M_2$ and $RNH(CH_2)_m CO_2 M$, where m varies from 1 to 4, R is $C_8$-$C_{30}$ alkyl; preferably, $C_{12}$-$C_{22}$ alkyl, and M is H, alkali metal, alkaline earth metal ammonium, or alkanolammonium.

Other suitable amphoteric and zwitterionic surfactants are imidazolinium and ammonium derivates. Suitable examples of such amphoteric surfactants include sodium 3-dodecyl-aminopropionate, sodium 3-dodecylaminopropane sulfonate, N-alkyltaurines; N-higher alkyl aspartic acids, and coamidopropyl PG-dimonium chloride phosphate. For further examples of suitable amphoteric and zwitterionic surfactants, please see U.S. Pat. Nos. 2,658,072, 2,438,091, and 2,528,378, which are incorporated herein by reference Yet other suitable amphoteric and zwitterionic surfactants are betaines. Examples of suitable betaines include coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl) alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl)sulfopropyl betaine, and amidobetaines and amidosulfobetaines, oleyl betaine, and cocamidopropyl betaine.

PROPELLANTS

A propellant is one of the additional ingredients mentioned above which may be included in the present invention. Propellants are chemicals used for expelling products from pressurized containers (aerosols). They can be used in connection with, for example, mousses and aerosol sprays. The functionality of a propellant depends on its vapor pressure at ambient temperature and its compressibility. Liquids or gases can be used as propellants as long as the pressure developed within the container is safely below the container's bursting pressure under normal storage and use conditions.

The examples of suitable propellants include butane, carbon dioxide, dimethyl carbonate, dimethyl ether, ethane, hydrochlorofluorocarbon 22, hydrochlorofluorocarbon 142b, hydrofluorocarbon 134a, hydrofluorocarbon 152a, hydrofluorocarbon 227ea, isobutene, isopentane, nitrogen, nitrous oxide, pentane, propane and mixtures thereof. In one embodiment, the most preferred propellant is a mixture of isobutene and propane, which is also known in the industry as Propellant A-46.

In one embodiment of the present invention, a propellant is present in a product composition in the amount that may vary from 5% to 20%, preferably from 7% to 10% relative to the total weight of the composition.

ADDITIONAL INGREDIENTS

The compositions of the invention may also include a wide range of additional ingredients. Some suitable additional ingredients commonly used in the cosmetic and personal care industry are described in The International Cosmetic Ingredient Dictionary and Handbook, ($9^{th}$ Ed., 2002), which is incorporated by reference herein.

The additional ingredients of the compositions of the invention may also include one or more absorbents, antifoaming agents, antimicrobial agents, antidandruff agents, binders, buffers, biological additives, buffering agents, bulking agents, chelating agents, chemical additives, coupling agents, conditioners, colorants, denaturants, detergents, dispersants, external analgesics, film formers, foaming agents, fragrance components, humectants, opacifying agents, pH adjusters, preservatives, propellants, proteins, reducing agents, sequestrants, softeners, solubilizing agents, lubricants, penetrants, plasticizers, solvents and co-solvents, sunscreening additives, salts, essential oils, and vitamins.

Depending on the application, the amount of additional ingredient(s) present in the present invention may vary considerably, if present at all. In one embodiment of the present invention, the amount of additional ingredient(s) ranges from about 0.01% to about 10% relative to the total weight of the composition, preferably from about 0.1% to about 5% relative to the total weight of the composition.

ADJUVANTS

The compositions of the present invention may also contain adjuvants suitable for hair care. Suitable hair care adjuvants include, but are not limited to:

Natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts. A particularly preferred combination of natural hair root nutrients for inclusion in compositions of the invention is isoleucine and glucose. A particularly preferred amino acid nutrient is arginine.

Nonvolatile silicone compounds may also be employed as adjuvants in the present invention such as, for example, a polydimethylsiloxane, polyalkyl siloxane, a polyaryl siloxane or a polyalkylaryl siloxane. The nonvolatile silicones are nonfunctional siloxanes or siloxane mixtures having a viscosity of about 10 to about 10,000 cst , and most preferred viscosity about 10 to 500 cst at 25° C. A nonvolatile silicone compound is described as having a boiling point at atmospheric pressure of greater than about 250° C. A particularly preferred nonvolatile silicone compound is cyclopentasiloxane, commercially available from Dow Corning under the tradename DC 245.

Additional adjuvants include gelling agents, waxes, preservatives, suspending agents, volatile solvents, thickening agents, film formers, spreading agent, dispersants, antifoaming agents, wetting agents, UV-screening agents, antioxidants, perfumes, fillers, active agents, moisturizers, vitamins, biological materials, and derivatives of any of the foregoing.

The present invention provides a novel process for imparting a color onto a keratinous substrate comprising contacting a keratinous substrate with a cosmetic composition containing at least one triarylmethane dye molecule chosen from polymeric triarylmethane dye molecules, copolymeric triarylmethane dye molecules, oligomeric triarylmethane dye molecules, and mixtures thereof, at least one film forming agent, and at least one solvent, and irradiating the treated keratinous substrate with a flash of light to impart a change in color and/or enhanced shine on the said substrate. This process facilitates the styling of substrates, such as hair, in a cosmetically appealing manner.

EXAMPLES

The following examples illustrate the subject matter of the invention in further detail. All exemplified amounts are concentrations by weight of the total composition, unless otherwise specified.

Formulas:

TABLE 1

Gel formula

| Ingredients | Percentage (%) |
|---|---|
| BASAZOL C-VIOLET PR8055 | 1.50 |
| Guar hydroxypropyltrimonium chloride | 1.00 |
| Water | 97.50 |

TABLE 2

Mousse formula

| Ingredients | Percentage (%) |
|---|---|
| BASAZOL C-VIOLET PR8055 | 0.094 |
| Guar hydroxypropyltrimonium chloride | 0.35 |
| Sodium/magnesium laureth-8 sulfate | 0.19 |
| Sodium/magnesium oleth sulfate | |
| Isobutane/propane | 6.00 |
| water | q.s. to 100.00 |

The combination of the oligomeric triarylmethane dye and film-forming polymer in a solvent were tested to show the color change that occurs upon exposure to a flash of light. The original color of the coating was yellow-gold whereas the flash-light induced color was violet.

Salon-Testing Results

The invention was tested on 6 models with dark-straight hair. The gel and mousse formulas were applied on hair using a conventional hair brush. The hair was then dried by use of a rotating drier and evaluated based on the shine, color and other cosmetic properties. The results are listed in the following:

TABLE 1

Gel formula

| Amount (grams) | Hair (original color) | Observations after applying the formula onto hair |
|---|---|---|
| 1.5 | dark brown | Easy to comb, slight-transfer; shine<br>Before flash: dark blonde color<br>After flash: purple color |
| 2.2 | dark brown | Easy to comb, slight-transfer; shine<br>Before flash: light brown color<br>After flash: purple color |
| 3.0 | darkest brown | Easy to comb, slight-transfer; shine<br>Before flash: dark blonde color<br>After flash: purple color |

TABLE 2

Mousse formula

| Amount (grams) | Hair (original color) | Observations after applying the formula onto hair |
|---|---|---|
| 1.1 | black | Good manageability, slight-transfer, shine<br>Before flash: light brown color<br>After flash: purple color |
| 2.2 | medium brown | Easy to comb, slight-transfer, shine<br>Before flash: dark blonde color<br>After flash: purple color |
| 2.7 | medium brown | Easy to comb, slight-transfer, shine<br>Before flash: dark blonde color<br>After flash: purple color |

The formulation examples above were formulated by mixing an oligomeric triarylmethane dye and a film forming agent in a solvent, and then optionally admixing it with a propellant. Upon application to a keratinous substrate and exposure to a flash of light, the cosmetic compositions demonstrated a change in color of the treated hair and enhanced shine.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A process for imparting color onto a keratinous substrate comprising:
   (a) providing a keratinous substrate;
   (b) providing a cosmetic composition containing:
      (i) at least one triarylmethane dye molecule chosen from polymeric triarylmethane dye molecules, copolymeric triarylmethane dye molecules, oligomeric triarylmethane dye molecules, and mixtures thereof;
      (ii) at least one film forming agent; and,
      (iii) at least one solvent,
   (c) contacting the keratinous substrate with the cosmetic composition to form a treated keratinous substrate; and,
   (d) irradiating the treated keratinous substrate with a flash of light.

2. The process of claim 1, wherein said at least one triarylmethane dye molecule is an oligomeric triarylmethane.

3. The process of claim 1 wherein said at least one triarylmethane dye molecule is chosen from Basic Violet Acetate, Basic Blue Acetate, and mixtures thereof.

4. The process of claim 1, wherein said at least one triarylmethane molecule is present in an amount ranging from about 0.05% to about 2% by weight, relative to the total weight of said cosmetic composition.

5. The process of claim 1, wherein said at least one triarylmethane molecule is present in an amount ranging from about 0.075% to about 1% by weight, relative to the total weight of said cosmetic composition.

6. The process of claim 1, wherein said at least one film forming agent is chosen from anionic, non-ionic, cationic, and amphoteric agents.

7. The process of claim 6, wherein said at least one film forming agent is a di-block, tri-block, multi-block or radial copolymer.

8. The process of claim 1, wherein said at least one film forming agent is an imide based copolymer.

9. The process of claim 8, wherein said imide based copolymer is Polyimide-1 or Isobutylene/Ethylmaleimide/Hydroxyethylmaleimide Copolymer.

10. The process of claim 1, wherein said film forming agent is a sulfonate based copolymer.

11. The process of claim 10, wherein said sulfonate based copolymer is chosen from Acrylamide/Sodium Acryloyldimethyltaurate/Acrylic Acid Polymer, sodium polystyrene sulfonate and polyester-5.

12. The process of claim 1, wherein said at least one film forming agent is present in an amount ranging from about 1% to about 20% by weight, relative to the total weight of said cosmetic composition.

13. The process of claim 1 wherein said at least one solvent is selected from an organic solvent, water and a mixture thereof.

14. The process of claim 1, wherein said at least one solvent is ethanol.

15. The process of claim 1, wherein said at least one solvent is present in an amount ranging from about 75% to about 99% by weight, relative to the total weight of said cosmetic composition.

16. The process of claim 1, further comprising a surfactant.

17. The process of claim 16, wherein said surfactant is chosen from magnesium laureth sulfate, sodium laureth sulfate, and mixtures thereof.

18. The process of claim 16, wherein said surfactant is present in an amount ranging from about 0.05% to about 5% by weight, relative to the total weight of the composition.

19. The process of claim 1, further comprising a propellant.

20. The process of claim 19, wherein said propellant is an Isobutane/Propane mixture.

21. The process of claim 19, wherein said propellant is present in an amount ranging from about 0.01% to about 6% by weight, relative to the total weight of the composition.

* * * * *